US012582453B2

(12) United States Patent
Seykora et al.

(10) Patent No.: US 12,582,453 B2
(45) Date of Patent: Mar. 24, 2026

(54) ANTEROLATERAL CLAVICLE FRACTURE FIXATION PLATE

(71) Applicant: Acumed LLC, Hillsboro, OR (US)

(72) Inventors: Andrew W. Seykora, Portland, OR (US); Brian Schultz, Camp Sherman, OR (US); Bruce Ziran, Decatur, GA (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 17/698,360

(22) Filed: Mar. 18, 2022

(65) Prior Publication Data

US 2022/0296288 A1     Sep. 22, 2022

Related U.S. Application Data

(60) Provisional application No. 63/164,274, filed on Mar. 22, 2021.

(51) Int. Cl.
    *A61B 17/80*          (2006.01)

(52) U.S. Cl.
    CPC ...... *A61B 17/8076* (2013.01); *A61B 17/8052* (2013.01)

(58) Field of Classification Search
    CPC . A61B 17/80; A61B 17/8052; A61B 17/8061; A61B 17/8076; A61B 17/808
    See application file for complete search history.

(56) References Cited

U.S. PATENT DOCUMENTS

| | | | | |
|---|---|---|---|---|
| 8,834,532 B2 * | 9/2014 | Velikov | .................. | A61B 17/80 |
| | | | | 606/280 |
| 11,207,111 B2 * | 12/2021 | Zenker | .............. | A61B 17/8061 |

(Continued)

FOREIGN PATENT DOCUMENTS

| | | |
|---|---|---|
| CN | 107007342 A | 8/2017 |
| EP | 3372181 A1 | 9/2018 |

(Continued)

OTHER PUBLICATIONS

International Search Report corresponding to related International Patent Application No. PCT/US2022/021008 mailed Jun. 9, 2022, 3 pages.

(Continued)

*Primary Examiner* — Si Ming Ku
(74) *Attorney, Agent, or Firm* — Knobbe, Martens, Olson & Bear, LLP

(57)          ABSTRACT

The present application provides new and innovative anterior clavicle plates and systems for clavicle fracture fixation. The provided anterior clavicle plate is shaped to better conform to or fit the anterior and lateral surfaces of a patient's clavicle as compared to typical anterior clavicle plates. This improved conformance can help reduce the incidence of tissue irritation, which reduces the chances of a second surgery being needed for removal of the anterior clavicle plate. The improved conformance can also result in an anatomically better fracture reduction than typical anterior clavicle plates and an increased fixation strength. Additionally, an instrument provided by the present application can help a surgeon install the provided anterior clavicle plate more quickly and with increased flexibility and consistency than typical systems.

20 Claims, 16 Drawing Sheets

(56)                References Cited

U.S. PATENT DOCUMENTS

| | | | |
|---|---|---|---|
| 2009/0076554 A1* | 3/2009 | Huebner | A61B 17/1684 |
| | | | 606/280 |
| 2011/0160730 A1* | 6/2011 | Schonhardt | A61B 17/085 |
| | | | 606/71 |
| 2012/0059424 A1* | 3/2012 | Epperly | A61B 17/8061 |
| | | | 606/280 |
| 2013/0238032 A1 | 9/2013 | Schilter | |
| 2014/0172020 A1* | 6/2014 | Gonzalez-Hernandez | |
| | | | A61B 17/8085 |
| | | | 606/280 |
| 2015/0223824 A1* | 8/2015 | Mebarak | A61B 17/1728 |
| | | | 606/87 |
| 2016/0346022 A1 | 12/2016 | Price et al. | |
| 2017/0215931 A1* | 8/2017 | Cremer | A61B 17/8052 |
| 2018/0256224 A1* | 9/2018 | Govey | A61B 17/8004 |
| 2019/0183549 A1 | 6/2019 | Singh | |
| 2019/0365437 A1 | 12/2019 | Lueth et al. | |
| 2022/0110665 A1 | 4/2022 | Laird et al. | |

FOREIGN PATENT DOCUMENTS

| | | | |
|---|---|---|---|
| EP | 3533402 | A1 | 9/2019 |
| JP | 2017-196469 | A | 11/2017 |
| JP | 2018-171433 | A | 11/2018 |
| JP | 2019-171029 | A | 10/2019 |
| JP | 2021-506559 | A | 2/2021 |
| WO | WO 2013/170164 | A1 | 11/2013 |
| WO | WO 2022/203967 | A1 | 9/2022 |

OTHER PUBLICATIONS

International Written Opinion corresponding to related International Patent Application No. PCT/US2022/021008 mailed Jun. 9, 2022, 6 pages.

International Preliminary Report on Patentability, re PCT Application No. PCT/US2022/021008, dated Oct. 5, 2023.

* cited by examiner

ANTEROLATERAL CLAVICLE FRACTURE FIXATION PLATE

PRIORITY CLAIM

The present application claims priority to and the benefit of U.S. Provisional Application 63/164,274, filed Mar. 22, 2021, the entirety of which is herein incorporated by reference.

BACKGROUND

One issue that can arise in clavicle fracture fixation is tissue irritation resulting from the fixation hardware. In some instances, this tissue irritation can lead to a second surgery to remove the fixation hardware. Installing a plate on the superior surface of a clavicle is one method used by surgeons for clavicle fracture fixation that can lead to such tissue irritation. While superior clavicle plates offer desired lateral fixation, one technique that can help reduce the chances of a second surgery being needed is the use of anterior clavicle plates for fracture fixation. Anterior clavicle plates can also provide improved lateral purchase over superior clavicle plates as screws can be substantially longer when running anterior to posterior through the clavicle, as compared to running superior to inferior.

Typical anterior clavicle plates, however, have a less than desired fit or conformance on the anterior and lateral surfaces of a patient's clavicle, which can increase the incidence of tissue irritation and/or limit the amount of fixation that the plate can provide. Accordingly, an anterior clavicle plate with a more conforming fit to a patient's clavicle than typical anterior clavicle plates is desired.

SUMMARY

The present application provides new and innovative anterior clavicle plates and systems for clavicle fracture fixation. The provided anterior clavicle plate enables a more conforming fit to a patient's clavicle than typical anterior clavicle plates, which can help reduce the incidence of tissue irritation and increase clavicle fracture fixation strength.

In an example, an anterior clavicle fracture fixation plate includes a contoured body having a first end opposite a second end, a superior side opposite an inferior side, and multiple openings along a length of the contoured body from the first end to the second end. A plane extends through a first portion of the contoured body, the first portion being adjacent the first end, and a second portion of the contoured body curves away from the plane in a first direction, the second portion of the contoured body being adjacent the second end. The contoured body includes a first bend along its length that bends at least partially in a second direction perpendicular to the first direction. A height of the contoured body, measured perpendicular to the length, is greater at the first end than at the second end. A cross-section of the contoured body is curved from the superior side to the inferior side.

In another example, a system for clavicle fracture fixation includes the above example anterior clavicle fracture fixation plate and an instrument configured to aid in insertion of one or more screws through openings of the anterior clavicle fracture fixation plate on an anterior surface of a clavicle.

In another example still, a method for fixing a fracture of a clavicle includes installing the above example anterior clavicle fracture fixation plate on at least an anterior surface of the clavicle. Installing the anterior clavicle fracture fixation plate includes inserting respective screws through each of the plurality of openings of the anterior clavicle fracture fixation plate and into the clavicle.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

DETAILED DESCRIPTION

The present application provides new and innovative anterior clavicle plates and systems for clavicle fracture fixation. The presently disclosed anterior clavicle plate is shaped to better conform to or fit the anterior and lateral surfaces of a patient's clavicle as compared to typical anterior clavicle plates. This improved conformance can help reduce the incidence of tissue irritation, which reduces the likelihood that a second surgery is needed to remove the anterior clavicle plate. The improved conformance can also result in an anatomically better fracture reduction than typical anterior clavicle plates and in an increased fixation strength. An additional advantage of the provided anterior clavicle plate and system can be faster installation compared to typical anterior clavicle plates, which reduces surgical procedures lengths. For instance, the improved conformance can help limit how much a surgeon may need to adjust the provided anterior clavicle plate prior to inserting the screws. Additionally, an instrument provided by the present application can help a surgeon install the provided anterior clavicle plate more quickly and with increased flexibility and consistency than typical systems. The shape of the presently disclosed anterior clavicle plate that enables the improved conformance will be described in the description of the figures below in comparison to typical anterior clavicle plates.

Figure 1:
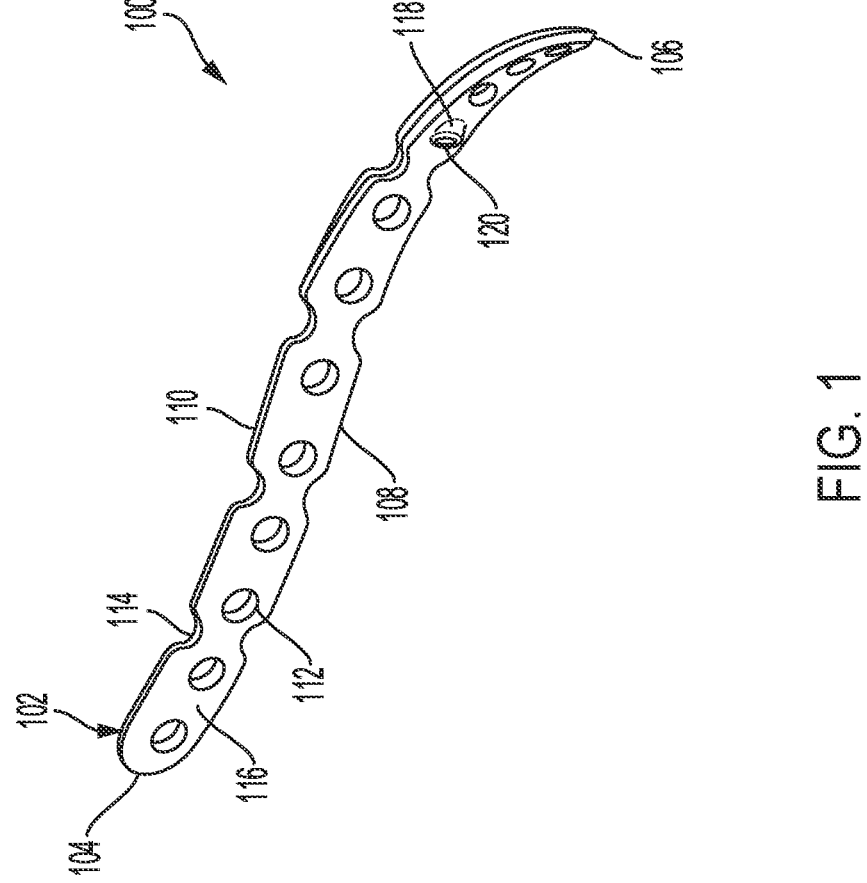
FIG. 1 illustrates a perspective view of an anterior clavicle fracture fixation plate, according to an aspect of the present disclosure.
Figure 2:
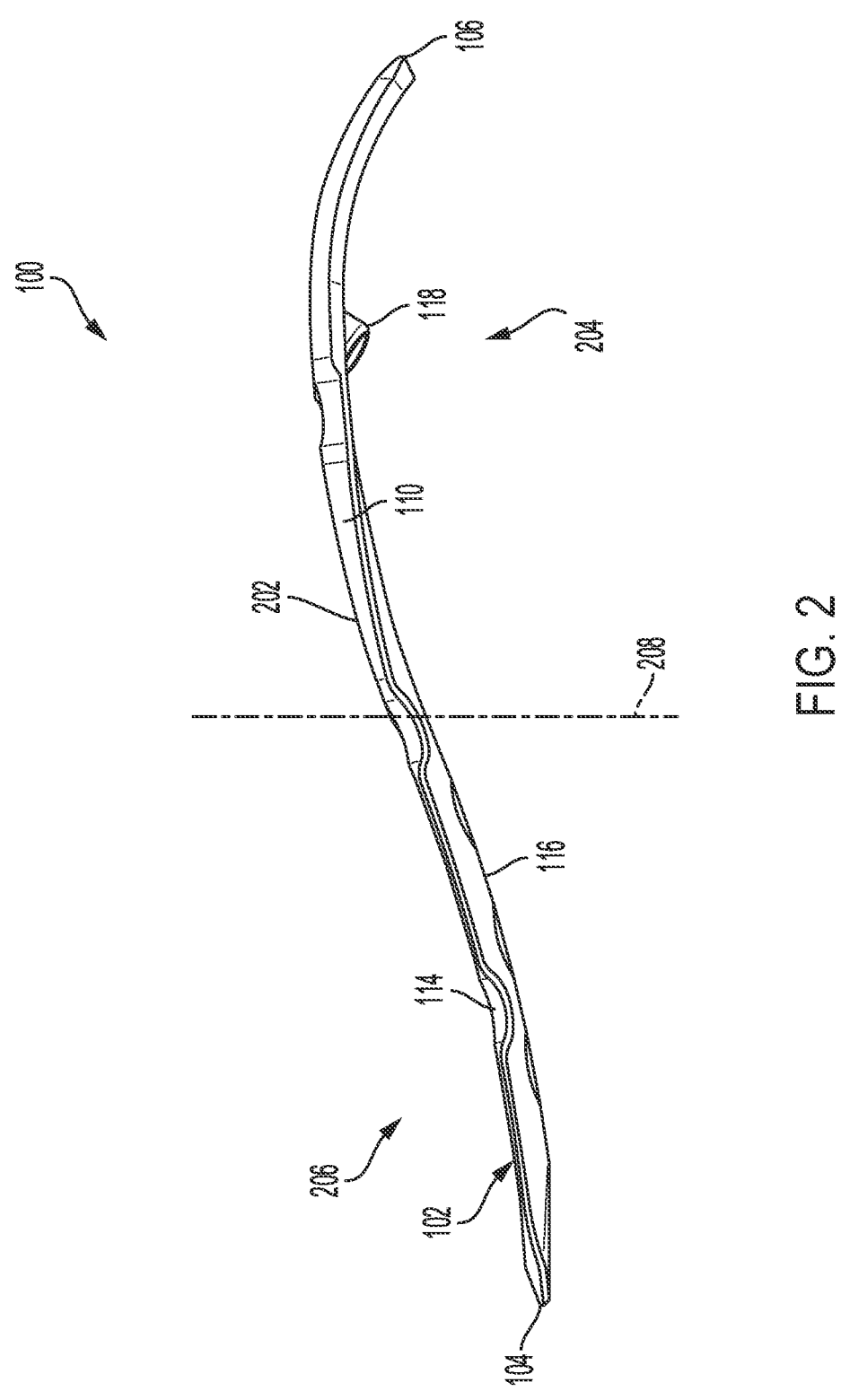
FIG. 2 illustrates a top view of the anterior clavicle fracture fixation plate of FIG. 1, according to an aspect of the present disclosure.
Figure 3:
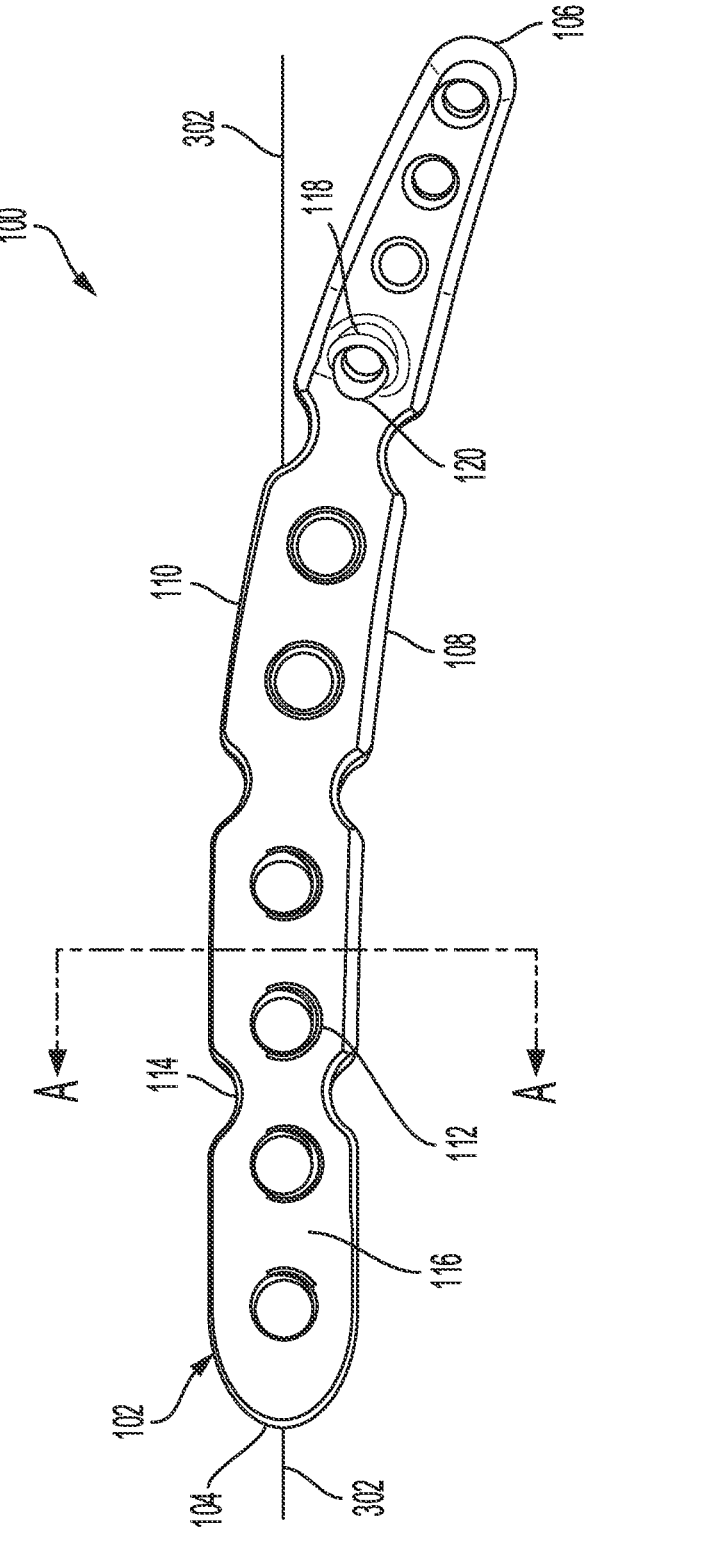
FIG. 3 illustrates a front view of the anterior clavicle fracture fixation plate of FIG. 1, according to an aspect of the present disclosure.
Figure 4:
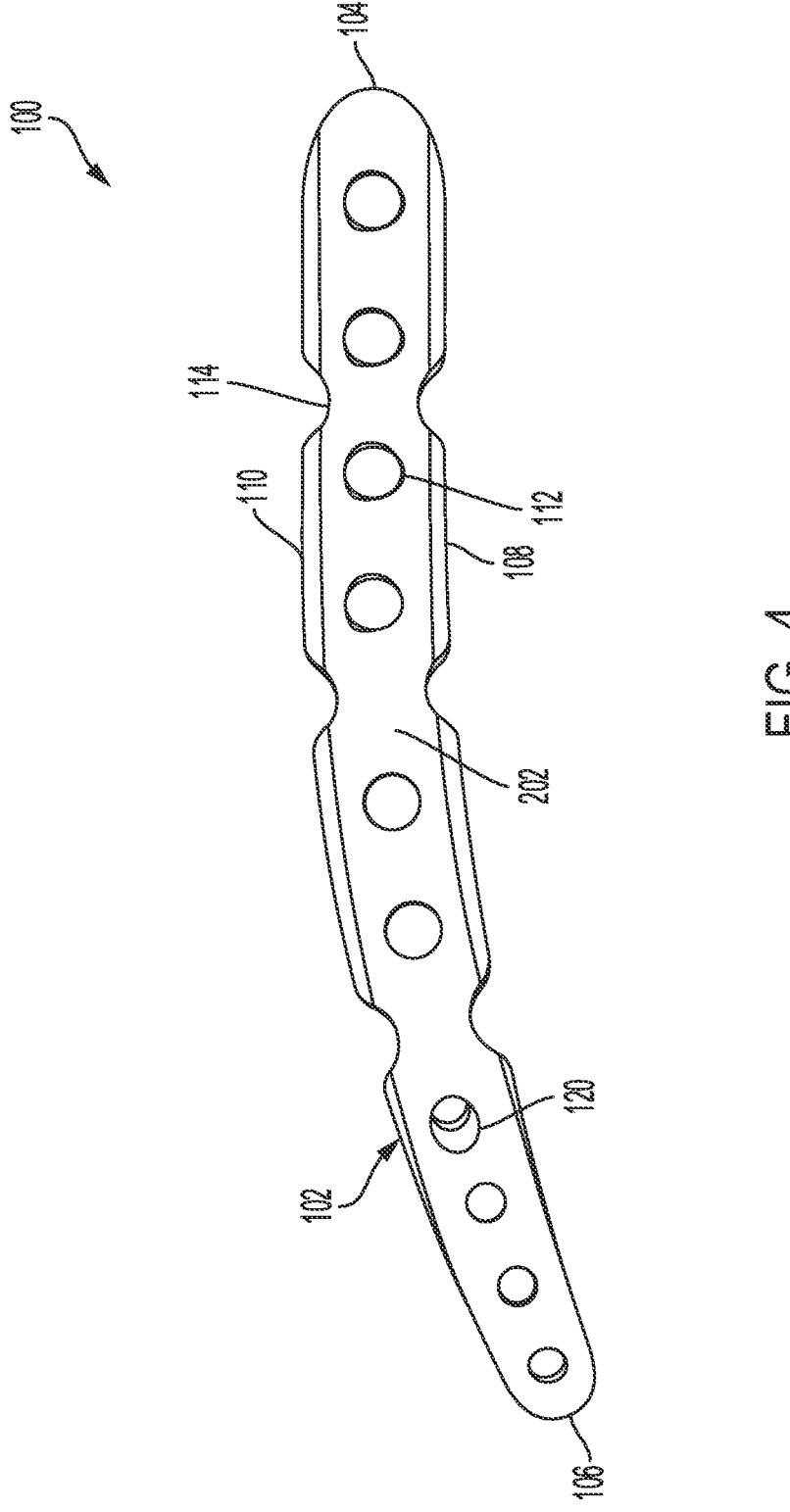
FIG. 4 illustrates a back view of the anterior clavicle fracture fixation plate of FIG. 1, according to an aspect of the present disclosure.

FIGS. 1 to 5 illustrate various views of an example anterior clavicle plate 100 to show the various aspects of the shape of the anterior clavicle plate 100. FIG. 1 illustrates a perspective view of the example anterior clavicle plate 100. The anterior clavicle plate 100 includes a contoured body 102. The contoured body 102 can be constructed of a suitable medical-grade material, such as a metal. For example, a suitable metal may be titanium or stainless steel. Another example suitable material may be carbon fiber reinforced PEEK. The contoured body 102 includes a first end 104 opposite a second end 106. The contoured body 102 includes a superior side 110 opposite an inferior side 108. The superior side 110 and the inferior side 108 each extend the entire length of the contoured body 102. The contoured body 102 also includes an exterior face 116 opposite an interior face 202 (FIGS. 2 and 4).

The contoured body 102 is shaped/contoured such that it is left or right specific. Stated differently, the contoured body 102 is shaped/contoured such that it conforms to a patient's right clavicle or the patient's left clavicle, but not both. The illustrated example contoured body 102 is shaped for a left-specific anterior clavicle plate 100. It should therefore be appreciated that a right-specific clavicle plate 100 includes a contoured body 102 that is a mirror image of the illustrated contoured body 102.

The contoured body 102 includes multiple openings 112 along a length of the contoured body 102 from its first end 104 to its second end 106. In some aspects, the multiple openings 112 can include at least one opening 120 that is angled with respect to the contoured body 102 at a different angle than the remaining openings 112. In some examples of such aspects, the contoured body 102 may include a guide

118 for each of the at least one opening 120. In such examples, the guide 118 can help assist in the insertion of a screw at an acute or obtuse angle relative to the contoured body 102. The opening 120 and the guide 118 are described in connection with FIG. 7 below. Only a single opening of the openings 112, aside from the opening 120, is indicated with a reference numeral in the figures solely for illustrative clarity, and therefore the description of the openings 112 applies equally to the other illustrated openings. Screws may be inserted through the openings 112 to secure the anterior clavicle plate 100 to a clavicle. In some aspects, the openings 112 may include threading that can engage with threading of a screw. Further description of the openings 112 is given with the description of FIG. 3 below.

In some aspects, the contoured body 102 may include at least one reduced portion 114 with respect to a height of the contoured body 102. For example, the contoured body 102 illustrated in FIG. 1 includes four reduced portions 114. In other examples, the contoured body 102 may include more or less reduced portions 114. The reduced portions 114 can help prevent stress raisers at the openings 112. The reduced portions 114 can also help enable the plate to bend at the reduced portions 114 (e.g., the two portions adjacent a reduced portion 114 can be brought towards one another to a degree) so that a surgeon can better fit the plate to the contour of a bone.

FIG. 2 illustrates a top view of the example anterior clavicle plate 100. The top view of the anterior clavicle plate 100 best illustrates the curvature of the contoured body 102 in the anterior and posterior directions along its length from its first end 104 to its second end 106. For example, between the dashed line 208 and the second end 106, the contoured body 102 includes a first bend 204, and between the first end 104 and the dashed line 208, the contoured body 102 includes a second bend 206. The first bend 204 bends at least partially in a direction opposite of the direction of bend of the second bend 206, as illustrated. As used herein, a direction of a bend or curve refers to a direction of a radius of the curve or bend at a given point on the curve or bend. The first bend 204 and the second bend 206 do not bend in directly opposing directions due to curvature of the contoured body 102 in the inferior direction (e.g. into the page in FIG. 2) nearest the second end 106, as is best illustrated in FIGS. 3 and 4 discussed below.

In some aspects, the first bend 204 includes an inconsistent or asymmetric radius of curvature. For example, the radius of curvature of the first bend 204 may be greater nearer to the second end 106 than towards the middle portion (e.g., the dotted line 208) of the length of the contoured body 102. In some aspects, the second bend 206 may have a consistent or symmetric radius of curvature. In other aspects, the second bend 206 may have an inconsistent or asymmetric radius of curvature. The above-described curvature along the length of the contoured body 102 helps the anterior clavicle plate 100 conform to the anatomy of a patient's left clavicle. For example, the increased radius of curvature of the first bend 204 nearer to the second end 106 can help the anterior clavicle plate 100 conform to the lateral portion of the patient's left clavicle.

FIG. 3 illustrates a front view of the example anterior clavicle plate 100. The plane A-A shown in FIG. 3 will be referenced in connection with FIG. 5 below. The front view of the anterior clavicle plate 100 best illustrates the curvature of the contoured body 102 in the inferior direction along its length. For instance, a plane 302 extends through only a portion of the contoured body 102 adjacent to the first end 104. Another portion of the contoured body 102 adjacent to the second end 106 curves away from the plane 302. In FIG.
3, the anterior and posterior curvature of the contoured body
102 (e.g., described in FIG. 2) is into and out of the page. As
such, at least a portion of the curvature of the contoured
body 102 in the inferior direction bends in a direction that is
perpendicular to at least a portion of the contoured body 102
anterior and/or posterior curvature.

Typical anterior clavicle plates do not include such infe-
rior curvature described above and shown in FIG. 3. A
patient's clavicle anatomy, however, typically does include
curvature in the inferior direction. Accordingly, typical
anterior clavicle plates do not conform to the anatomy of the
lateral portion of a patient's clavicle without a surgeon
flattening the patient's fractured clavicle or significantly
bending the typical anterior clavicle plate. Bending plates
takes operative time and also plastically deforms the plate,
which can lead to weakening and reduced fatigue life for the
plate. The presently disclosed anterior clavicle plate 100, by
having the above-described inferior curvature, reduces the
amount a surgeon must bend the anterior clavicle plate 100
to conform to the anatomy of the patient's clavicle because
the anterior clavicle plate 100 is initially closer to an average
patient anatomy than typical anterior clavicle plates. The
reduction in bending needed can help reduce operative time
and increase fatigue life of the anterior clavicle plate 100 as
compared to typical anterior clavicle plates.

Further, by having an initial inferior curvature that more
closely matches an average patient anatomy, the anterior
clavicle plate 100 can also help a surgeon more closely
conform the anterior clavicle plate 100 to the lateral portion
of the patient's clavicle anatomy as compared to typical
anterior clavicle plates, since less adjustment to the anterior
clavicle plate 100 is needed. The advantage of better con-
formance to the anatomy of the lateral portion of the
patient's clavicle helps ensure that fixation points (e.g.,
screws through the openings 112) are central to the patient's
clavicle to provide desired screw purchase in clavicle bone
and desired stability for the anterior clavicle plate 100.
Stated differently, the increased conformance helps the ante-
rior clavicle plate 100, upon installation, maintain fixation of
one or more clavicle fractures better than typical anterior
clavicle plates. The increased conformance can also help
ensure a more anatomic restoration of the patient's fractured
clavicle.

In some aspects, a height of the contoured body 102 may
change along its length from the first end 104 to the second
end 106. The height of the contoured body 102 is measured
from the outermost edge of the superior side 110 to the
outermost edge of the inferior side 108. In such aspects, as
best shown in FIG. 3, the height of the contoured body 102
is greatest towards the first end 104 and smallest towards the
second end 106. In some aspects, the height of the contoured
body 102 may gradually decrease along its length towards
the second end 106. The height differences of the contoured
body 102 can increase conformance with a clavicle because
the lateral portion of a clavicle's anterior surface tends to be
narrower than the clavicle's middle portion. In various
aspects, the height of the contoured body 102 decreases or
narrows in the region of the contoured body 102 that is
positioned against this narrower lateral portion of the clavi-
cle's anterior surface upon installation of the anterior
clavicle plate 100.

Also well illustrated in FIG. 3 are the multiple openings
112 on the contoured body 102. In various aspects, such as
the one illustrated, the openings 112 nearer to the first end
104 have larger diameters than the openings 112 nearer to
the second end 106. In at least some aspects, the region of the contoured body 102 nearest the second end 106 (e.g., the
region including the four nearest openings 112 from the
second end 106) is positioned at the lateral portion of a
patient's clavicle when the anterior clavicle plate 100 is
installed. A higher density of screws in the lateral portion of
the patient's clavicle, as compared to the middle or medial
portions of the patient's clavicle, can be helpful for clavicle
fracture compression. The smaller diameter openings 112
accommodate smaller screws, which enables a higher den-
sity of screws. The lateral portion of the patient's clavicle is
also narrower than the middle or medial portions and
therefore smaller diameter screws are more suitable to fit the
narrower bone, which the smaller diameter openings 112
accommodate.

FIG. 4 illustrates a back view of the example anterior
clavicle plate 100. The back view of the anterior clavicle
plate 100 helps illustrate the lateral curvature of the con-
toured body 102 with respect to a long axis that extends
through the center of the contoured body 102 along its
length. For instance, the portions of the contoured body 102
adjacent the openings 112 may extend into the page and the
inferior side 108 and superior side 110 may each extend out
of the page. This curvature aspect, however, is best illus-
trated in FIG. 5 described below.

Figure 5:
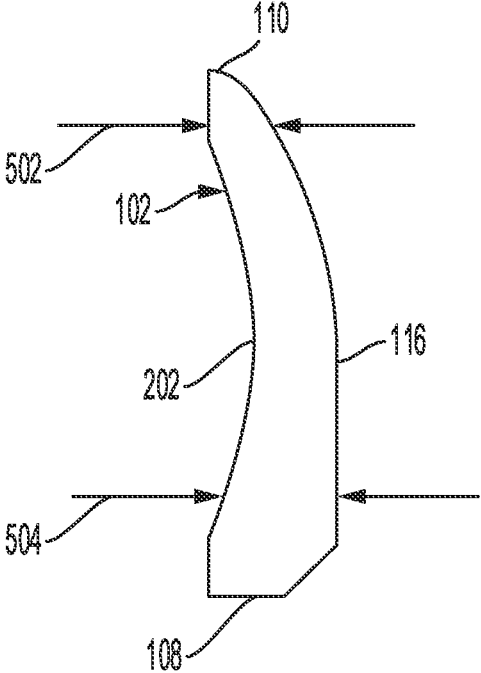
FIG. 5 illustrates a cross-sectional view of a portion of the anterior clavicle fracture fixation plate of FIG. 1, according to an aspect of the present disclosure.

FIG. 5 illustrates a cross-sectional view of the example
anterior clavicle plate 100 at the plane A-A shown in FIG.
3. The illustrated cross-sectional view of the anterior
clavicle plate 100 best illustrates the lateral curvature of the
contoured body 102 with respect to its above-described long
axis. For example, the exterior face 116 and the interior face
202 of the contoured body 102 are each curved. This lateral
curvature with respect to its long axis can help the interior
face 202 of the anterior clavicle plate 100 conform to the
lateral surface of a patient's clavicle.

One advantage of the provided anterior clavicle plate 100
is that the contoured body 102 has a reduced thickness in at
least some areas in which a low prominence is key to reduce
or avoid tissue irritation when installed in a patient. The
reduced thickness helps the anterior clavicle plate 100 be
low-profile when installed. The contoured body 102 also has
an increased thickness in at least some areas in which added
strength is beneficial. For example, the cross-sectional view
of the anterior clavicle plate 100 shown in FIG. 5 illustrates
a portion of the contoured body 102 adjacent the superior
side 110 having a thickness 502. A portion of the contoured
body 102 adjacent the inferior side 108 is shown having a
thickness 504. The thickness 502 is less than the thickness
504. Each of the thickness 502 and the thickness 504 are
measured perpendicular to the length of the contoured body
102 at any slice or cross-section (e.g., at the plane A-A) of
the contoured body 102. In at least some aspects, the
thickness 502 of the portion of the contoured body 102
adjacent the superior side 110 may be reduced as compared
to the body adjacent the superior side of at least some typical
anterior clavicle plates. In at least some aspects, the thick-
ness 504 of the portion of the contoured body 102 adjacent
the inferior side 108 may be greater than the body adjacent
the inferior side of at least some typical anterior clavicle
plates.

In some examples, a portion of the contoured body 102
adjacent the superior side 110 has a reduced thickness along
the entire length of the contoured body 102. In some aspects
of such examples, the thickness of the portion adjacent the
superior side 110 may gradually reduce from the first end
104 to the second end 106. In other aspects of such
examples, the portion adjacent the superior side 110 may
have segments of constant thickness and segments of reducing thickness. In other examples, only a segment of the length of the contoured body 102 includes a portion adjacent the superior side 110 having a reduced thickness, such as a segment adjacent the first end 104 and including the plane A-A.

The section(s) of the contoured body 102 having a portion adjacent the superior side 110 with a reduced thickness have a reduced strength. In an example, such as the one illustrated in FIG. 5, the portion adjacent the inferior side 108 in these section(s) of the contoured body 102 may have an increased thickness to counteract this reduction in strength at the superior side 110. In some examples, a portion of the contoured body 102 adjacent the inferior side 108 has an increased thickness along the entire length of the contoured body 102. In some aspects of such examples, the thickness of the portion adjacent the inferior side 108 may gradually increase along the contoured body 102 (e.g., the thickness of the portion adjacent the inferior side 108 gradually increases as the thickness of the portion adjacent the superior side 110 gradually decreases along the length of the contoured body 102). In other aspects of such examples, the portion adjacent the inferior side 108 may have segments of constant thickness and segments of increasing thickness. In other examples, only a segment of the length of the contoured body 102 includes a portion adjacent the inferior side 108 having an increased thickness.

Figure 6:
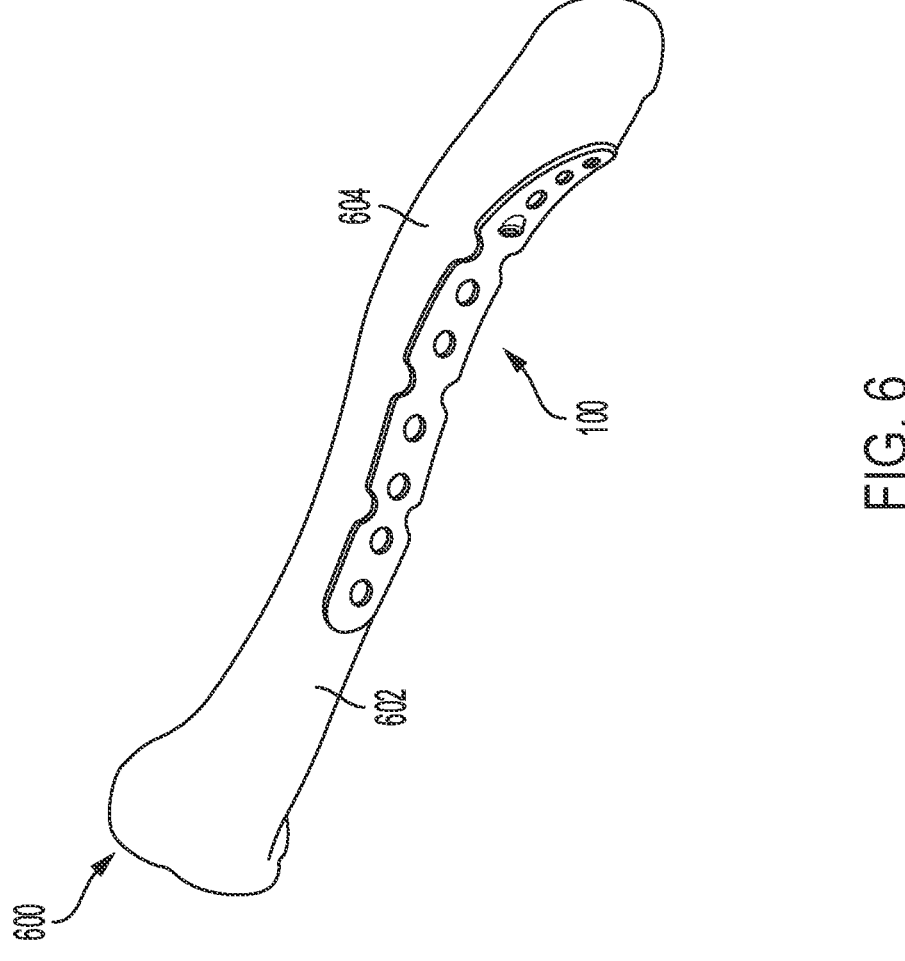
FIG. 6 illustrates a perspective view of an anterior clavicle fracture fixation plate positioned on an anterior surface of a clavicle, according to an aspect of the present disclosure.

FIG. 6 illustrates a perspective view of the anterior clavicle plate 100 positioned with respect to a clavicle 600, prior to the insertion of screws. The clavicle 600 is a left-side clavicle of a patient and includes an anterior surface 602 and a superior surface 604. As shown, the anterior clavicle plate 100 is positioned on the anterior surface 602 of the clavicle 600. In view of the above description of the shape/contour of the anterior clavicle plate 100, the contoured body 102 of the anterior clavicle plate 100 conforms to the contour of the anterior surface 602.

Figure 7A:
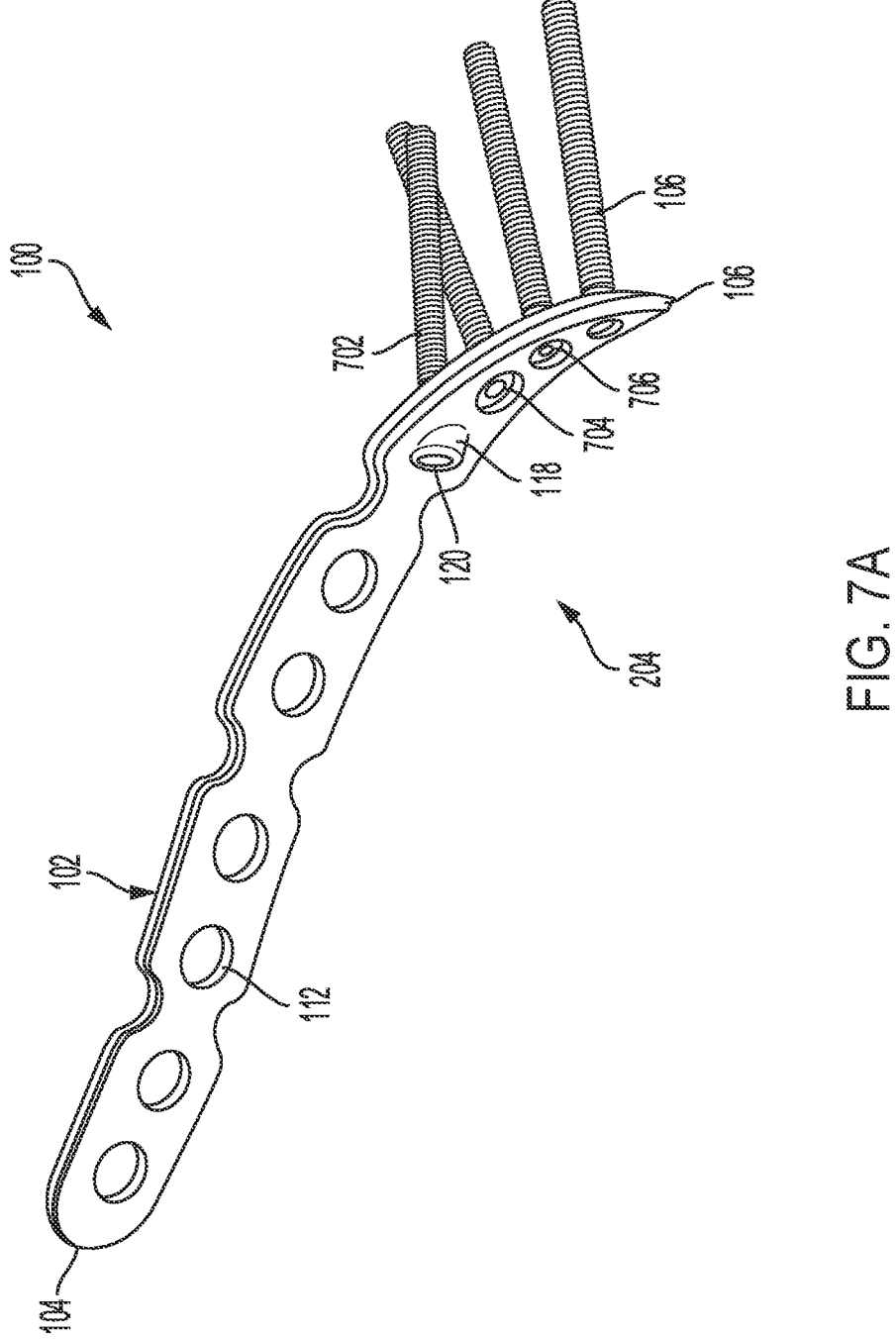
FIG. 7A illustrates a perspective view of an anterior clavicle fracture fixation plate having screws inserted through openings in a lateral portion of the plate, according to an aspect of the present disclosure.

FIG. 7A illustrates a perspective view of the anterior clavicle plate 100 having a screw 702 inserted through the opening 120 and screws 704-708 inserted through openings 112 in a lateral segment of the contoured body 102. When the anterior clavicle plate 100 is installed on a fractured clavicle, the screws 702-708 gain purchase into the clavicle to help fix the clavicle fragments and the anterior clavicle plate 100 to one another and promote healing by compressing one or more fractures. In various aspects, at least some of the openings 112 are configured such that a screw is substantially perpendicular to the contoured body 102 when inserted through a respective opening 112. For example, each of the screws 704, 706, and 708 are substantially perpendicular to the contoured body 102.

Figure 7B:
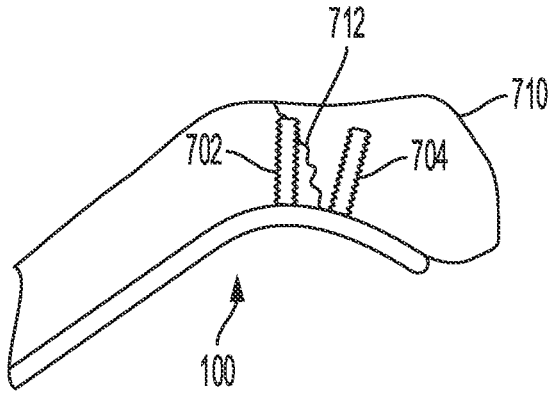
FIG. 7B illustrates a cross-sectional view of a fractured clavicle having a fracture line and an anterior clavicle plate without an angled opening, according to an aspect of the present disclosure.

It can be helpful for fracture compression to gain as much purchase across a fracture line with a screw as possible. It can be difficult in some instances, however, with a screw that is substantially perpendicular to the contoured body 102 to gain much, if any, purchase across a fracture line. For example, a fracture line at a clavicle's lateral bend can itself be substantially perpendicular, or near perpendicular (e.g., 60° to 80°), to the contoured body 102. FIG. 7B illustrates such an example. In FIG. 7B, a clavicle 710 includes a fracture with a fracture line 712. A screw 702 is substantially perpendicular to the contoured body 102 and is substantially parallel or near parallel with the fracture line 712. Therefore, only a small portion of the screw 702 can gain purchase across the fracture line 712. In other examples, the screw 702 might not gain purchase across any of a fracture line.

Returning to FIG. 7A, to help gain purchase across a fracture line that is substantially perpendicular, or near perpendicular, to the contoured body 102, in some aspects, the contoured body 102 includes at least one opening 120 configured such that a screw is at a non-perpendicular (i.e., acute/obtuse) angle to the contoured body 102 when inserted through such at least one opening 120. For example, the screw 702 is at an acute/obtuse angle to the contoured body 102. It should be appreciated that the screw 702 is illustrated in front of the screw 704 in FIG. 7A due to the inferior curvature of the contoured body 102 described above. In at least some aspects, the contoured body 102 may include a guide 118 protruding from the contoured body 102 at the opening 120 to aid in the insertion of the screw 702 at an acute/obtuse angle to the contoured body 102. For instance, without the guide 118, the angled nature of the opening 120 results in the interior perimeter of the opening 120, defined by the contoured body 102, having a greater surface area on one side as compared to the other. This difference in surface area of the opening 120 can make it difficult to insert the screw 702 concentrically with the opening 120. The guide 118 extends from the contoured body 102 to even out the surface area of the perimeter of the opening 120, which helps with inserting the screw 702 concentrically with the opening 120.

Figure 7C:
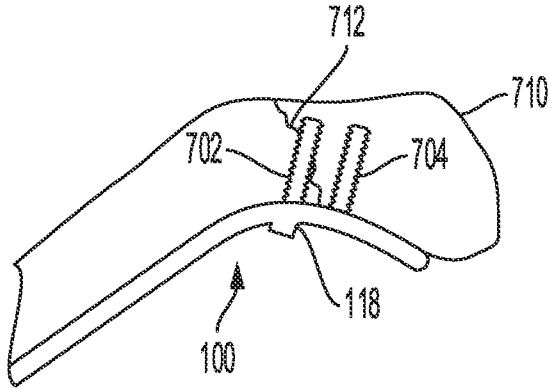
FIG. 7C illustrates a cross-sectional view of a fractured clavicle having a fracture line and an anterior clavicle plate having an angled opening, according to an aspect of the present disclosure.

The opening 120 can help gain purchase across a fracture line by enabling the screw 702 to approach the fracture line at a different angle than if the opening 120 was configured for the screw 702 to be substantially perpendicular to the contoured body 102 (e.g., configured as an opening 112 as in FIG. 7B). The approach angle enabled by the opening 120 helps a larger portion of the screw 702 gain purchase across the fracture line, as illustrated in FIG. 7C, which shows a larger portion of the screw 702 across the fracture line 712 as compared to FIG. 7B.

For the reasons mentioned above with respect to a fracture line at a clavicle's lateral bend, one or more openings 120 can be particularly helpful at the first bend 204 of the contoured body 102, which is positioned at a clavicle's lateral bend upon installation of the anterior clavicle plate 100. For example, the opening 120 shown in the example of FIG. 7 is located at the first bend 204 with three openings 112 between the second end 106 and the opening 120. In other examples, the contoured body 102 may include more than one opening 120 within the first bend 204 or may include one or more openings 120 outside of the first bend 204.

Figure 8A:
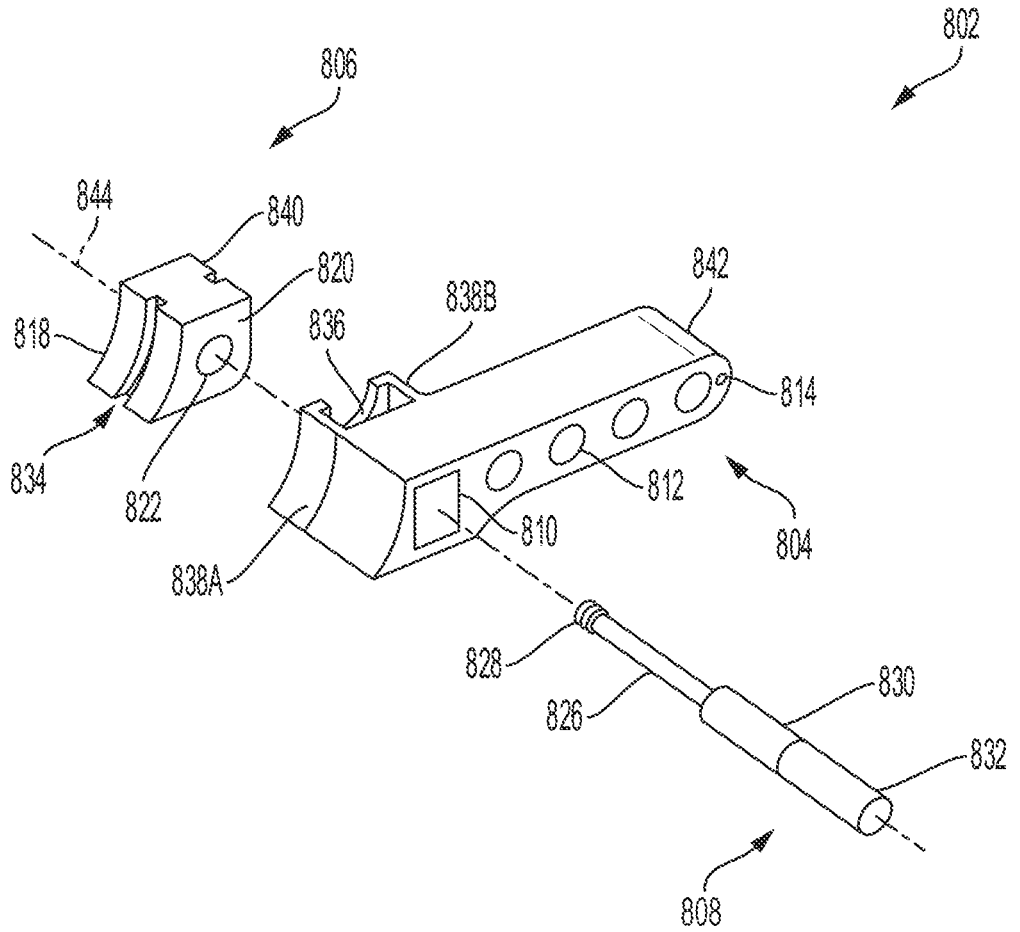
FIG. 8A illustrates an exploded view of an instrument for aiding in the installation of an anterior clavicle plate, according to an aspect of the present disclosure.

The present application additionally provides an insertion instrument that can aid the installation of the provided anterior clavicle plate (e.g., the anterior clavicle plate 100). FIG. 8A illustrates an exploded view of an example instrument 802. Drilling through the center of the clavicle when installing an anterior clavicle plate is preferred due to the clavicle's center being the longest portion of the clavicle, which enables the use of the longest screws possible for fixation. A longer screw provides greater fixation strength. Drilling, and thereafter installing a screw, through the clavicle's center can also help ensure a desired bone purchase. If the drill were to miss the center and exit the clavicle either superiorly or inferiorly, this would result in possible prominence of an installed screw and/or a shorter screw In some cases, however, it can be a challenge for a surgeon to drill through the center of a clavicle. For instance, surgeons typically use their eyes and fingers to judge a proper trajectory for a screw. At least some surgeons may additionally use a locking guide to help drill at their determined trajectory. A surgeon's determined trajectory using these methods, however, could be improved, such as the consistency with which the surgeon determines a trajectory through the center of the clavicle. The time it takes for a surgeon to determine the drilling trajectory for each of the openings 112 (and, in some instances, the opening 120) can also be reduced, which can help reduce surgical procedure times. The example instrument 802 can help surgeons make these improvements.

In various aspects, the instrument 802 includes a guide component 804, a base component 806, and a locking post 808. The guide component 804 includes a body 842 having a slot 810. The locking post 808 may be positioned through the slot 810 along the axis 844. In various aspects, the guide component 804 includes multiple openings 812 in the body 842. Only one opening of the multiple openings 812 is indicated with the reference numeral 812 solely for illustrative clarity, though it should be appreciated that the description of the openings 812 applies equally to each of the illustrated openings 812. Each of the openings 812 is configured to guide a drill through the opening 812. In some aspects, the guide component 804 may include an opening 814 in the body 842 configured to guide a k-wire or other suitable guidewire. In at least some aspects, the body 842 of the guide component 804 includes a curved or rounded surface 816 (best illustrated in FIG. 8B). The curved or rounded surface 816 may interface with the base component 806.

In some aspects, the guide component 804 includes wings 838A, 838B extending, integrally or fixedly, from the body 842. The wings 838A, 838B may each include an extension 836. For example, in some aspects the base component 806 may be removably coupled to the guide component 804 and the wings 838A, 838B may engage the base component 806 to do so. In other examples, the base component 806 may be fixedly coupled to the guide component 804, and in such other examples, the guide component 804 might not have the wings 838A, 838B.

In various aspects, the base component 806 includes a body 840 having a first surface 818 and a second surface 820. The first surface 818 may be shaped to interface with the exterior face 116 of the anterior clavicle plate 100. The second surface 820 may be curved or rounded, and interfaces with the curved or rounded surface 816 (FIG. 8B) of the guide component 804. In some examples, the body 840 of the base component 806 includes a notch 834 on opposing sides that each engage with the extensions 836 of the guide component 804 to couple the base component 806 to the guide component 804. In other examples, the base component 806 may be coupled to the guide component 804 with another suitable mechanism. In other examples still, the base component 806 might not include the notches 834, such as examples in which the base component 806 and the guide component 804 are fixedly coupled to one another. In at least some aspects, the base component 806 includes a channel 822 that extends through the guide component 804 from the first surface 818 to the second surface 820. In at least some aspects, a portion of the interior of the base component 806 in the channel 822 may include interior threading 846 (FIG. 8C). The locking post 808 may be positioned through the channel 822 along the axis 842.

In at least some aspects, the locking post 808 is shaped as a cylindrical rod. In various aspects, the locking post 808 includes a reduced portion 826 and a non-reduced portion 830. The reduced portion 826 is sized such that it may be positioned through the slot 810 of the guide component 804 and the channel 822 of the base component 806. At one end of the reduced portion 826, the locking post 808 includes an engagement end 828. For example, in some aspects, the engagement end 828 may be threaded. In such aspects, the threaded engagement end 828 may be adjustably engaged with threading of an opening 112 of the contoured body 102. For example, the further the threaded engagement end 828 is driven into an opening 112, the more threads of the threaded engagement end 828 and the opening 112 are engaged, and vice versa. This adjustable engagement helps control movement of the guide component 804, which is described below. In other aspects, the locking post 808 may be adjustably engaged with an opening 112 of the contoured body 102 via a suitable mechanism other than threading. In some aspects, the locking post 808 may include a grip or handle 832 at one end.

In at least some aspects, the non-reduced portion 830 of the locking post 808 is sized such that it cannot be translated through the slot 810 of the guide component 804 or the channel 822 of the base component 806. In some aspects, the engagement end 828 may be sized such that it cannot be translated through the slot 810 of the guide component 804 or the channel 822 of the base component 806. In examples in which the non-reduced portion 830 and the engagement end 828 are both so respectively sized, the guide component 804 and the base component 806 are coupled to the locking post 808 between the engagement end 828 and the non-reduced portion 830 of the locking post 808 when the instrument 802 is fully constructed. In some aspects, the guide component 804, the base component 806, and the locking post 808 are fixedly coupled to one another such that they cannot be decoupled. In such aspects, the reduced portion 826 may be positioned through the slot 810 during initial construction of the instrument 802. In other aspects, the guide component 804, the base component 806 and the locking post 808 can be separated from one another, for example, to be cleaned or sterilized. In such other aspects, the engagement end 828 may be sized such that it can be translated through the slot 810 and the channel 822.

Figure 8B:
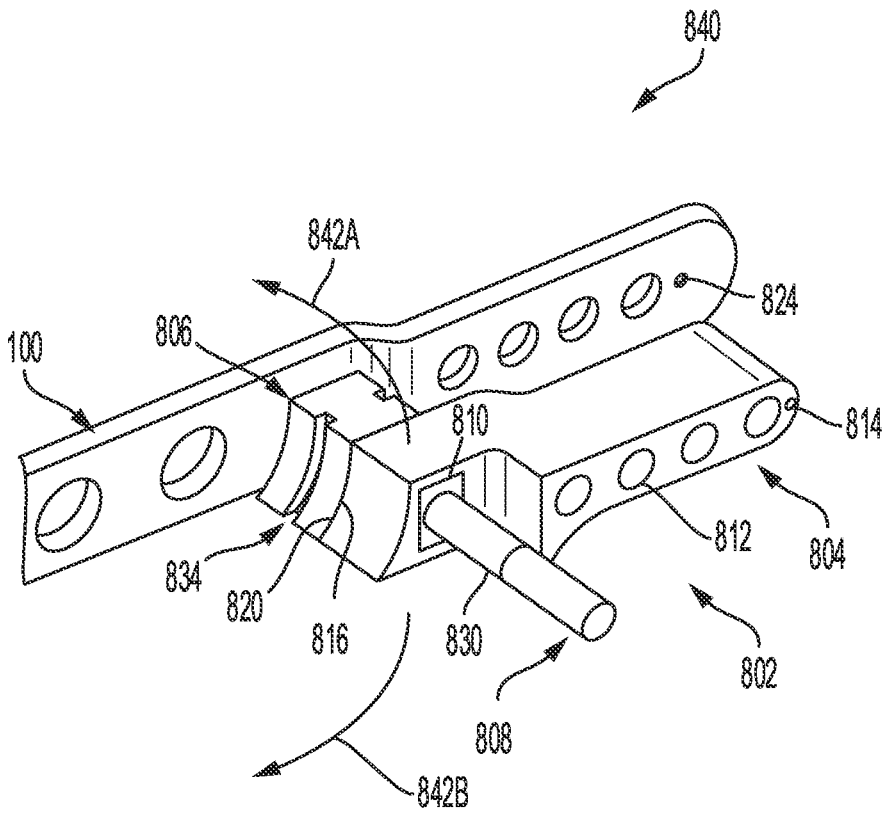
FIG. 8B illustrates a perspective view of a system including an anterior clavicle fracture fixation plate and an instrument for aiding in the installation of the plate, according to an aspect of the present disclosure.
Figure 8C:
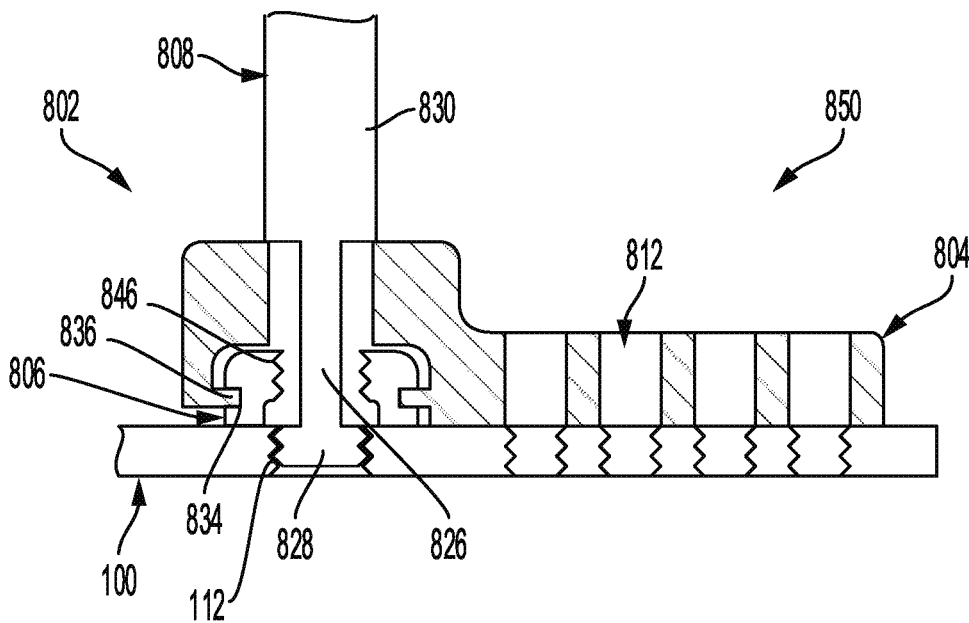
FIG. 8C illustrates a cross-sectional view of the system shown in FIG. 8B, according to an aspect of the present disclosure.

FIG. 8B illustrates an example system 850 including the anterior clavicle plate 100 and the fully constructed instrument 802. The wings 838A, 838B of the guide component 804 are not illustrated in FIG. 8B in order to illustrate the curved surface 816 of the guide component 804 interfacing with the second surface 820 of the base component 806. In this example, the engagement end 828 of the locking post 808 is threaded. To couple the instrument 802 to the anterior clavicle plate 100, a surgeon may first position the base component 806 in contact with the anterior clavicle plate 100 and over a threaded opening (e.g., an opening 112) of the anterior clavicle plate 100 such that the threaded engagement end 828 of the locking post 808 is aligned with the opening 112. Once positioned, the surgeon may advance the locking post 808 into engagement with the opening 112 (e.g., rotating the locking post 808 to engage the threading of the opening 112).

Upon initial engagement, the instrument 802 is coupled to the anterior clavicle plate 100, though the guide component 804 can still be adjusted. For example, the surgeon may rotate the guide component 804 about its long axis in the direction of the arrow 842A or the arrow 842B. The curved or rounded second surface 820 of the base component 806 and the curved or rounded surface 816 of the guide component 804 interface with one another as the guide component 804 is rotated. In an example, the surgeon may adjust the guide component 804 to a position at which the surgeon believes the openings 812 will guide screws into the center of the clavicle. Once the guide component 804 is at the surgeon's desired position, the surgeon may advance the locking post 808 further into engagement with the opening 112, thereby locking the guide component 804 in position.

The guide component 804 is locked in position due to the compressive force created between the anterior clavicle plate 100 and the non-reduced portion 830 of the locking post 808 by the engagement of the threaded engagement end 828 with the threaded opening 112.

FIG. 8C illustrates a cross-sectional view of the system 850 with the guide component 804 locked in position via the locking post 808. As shown, the extensions 836 of the guide component 804 are within the notches 834 of the base component 806. The engagement end 828 of the locking post 808 is engaged with the threaded opening 112 of the anterior clavicle plate 100. Further, the non-reduced portion 830 of the locking post 808 is contacted with the guide component 804, thereby compressing the base component 806 between the guide component 804 and the anterior clavicle plate 100.

As stated above, in at least some aspects, the base component 806 may include interior threading 846, which FIG. 8C illustrates. The interior threading 846 enables the guide component 804, base component 806, and locking post 808 to remain together as a single piece when the locking post 808 is disengaged from the threaded opening 112 of the anterior clavicle plate 100 by preventing the engagement end 828 from being translated through the base component 806. Rather, the locking post 808 must be rotated to engage and then disengage the engagement end 828 with the interior threading 846 to remove the locking post 808 from the base component 806 and thereafter from the guide component 804. Engaging the engagement end 828 with the interior threading 846 limits or prevents movement between the guide component 804, base component 806, and locking post 808 when the instrument 802 is disengaged from the anterior clavicle plate 100.

Maintaining the guide component 804, base component 806, and locking post 808 together when the instrument 802 is disengaged from the anterior clavicle plate 100 can be helpful for a surgeon so that one or more components do not fall into a patient's cavity during surgery, or onto the floor, when removing the instrument 802. Rather, the surgeon can hand the instrument 802 as a single piece to another medical professional. Maintaining the guide component 804, base component 806, and locking post 808 together can also be helpful for a surgeon when engaging the instrument 802 to the anterior clavicle plate 100. For instance, the engagement end 828 can be engaged with the interior threading 846 to help limit or prevent movement between the guide component 804, base component 806, and locking post 808 until the surgeon desires to adjust the instrument 802 when engaging it with the anterior clavicle plate 100.

Additionally, in at least some aspects, when the instrument 802 is positioned against the anterior clavicle plate 100, a pocket is formed between the interior threading 846 and the threaded opening 112. In such aspects, a surgeon may advance the engagement end 828 of the locking post 808 so that it is within this pocket, which enables the surgeon to adjust the instrument 802 prior to engaging the engagement end 828 with the threaded opening 112. It will be appreciated that FIG. 8C is not drawn to scale to show a pocket of a sufficient size to fit the engagement end 828, though consistent with the preceding disclosure, the pocket may be large enough to fit the engagement end 828.

Returning to FIG. 8B, with the guide component 804 locked in place, the surgeon may drive screws through each of the openings 812, through respective openings 112 in the anterior clavicle plate 100, and into the clavicle. In this way, the guide component 804 helps a surgeon avoid having to line up a trajectory for a screw for each opening 112 of the anterior clavicle plate 100. Instead, the surgeon lines up a trajectory once by adjusting the guide component 804, and then proceeds to insert each screw, which reduces the surgeon's installation time for the anterior clavicle plate 100, thereby reducing the surgical procedure time. The guide component 804 also helps increase the surgeon's screw trajectory consistency since the trajectory is consistent for each of the openings 812 with the guide component 804 locked in place.

In some instances, a surgeon may test the trajectory that the locked guide component 804 is providing at a given time through the use of the opening 814 sized to guide a k-wire or other suitable guidewire. For example, the surgeon may drill a k-wire through the opening 814 and into the clavicle. In some aspects of such an example, the anterior clavicle plate 100 may include an opening 824 that corresponds to the opening 814 and that enables the k-wire to be translated through the anterior clavicle plate 100 when drilling the k-wire into the clavicle. In other aspects, the opening 814 may be positioned on the guide component 804 such that a k-wire inserted through the opening 814 targets the clavicle outside the lateral end of the anterior clavicle plate 100 rather than going through the anterior clavicle plate 100.

With the k-wire inserted, the surgeon may image (e.g., a radiographic or fluoroscopic image) the clavicle to see the trajectory of the k-wire. If the surgeon is satisfied with the k-wire trajectory, the surgeon removes the k-wire and installs the screws. If the surgeon is not satisfied with the k-wire trajectory, the surgeon removes the k-wire, partially disengages the locking post 808, adjusts the guide component 804, and re-engages the locking post 808 to lock the guide component 804. In some instances, the surgeon may test the trajectory again. In other instances, the surgeon may be satisfied with the adjustment and installs the screws. In this way, the instrument 802 can help at least some surgeons improve their accuracy and/or consistency with which the surgeons insert screws at the center of the clavicle.

Figure 9A:
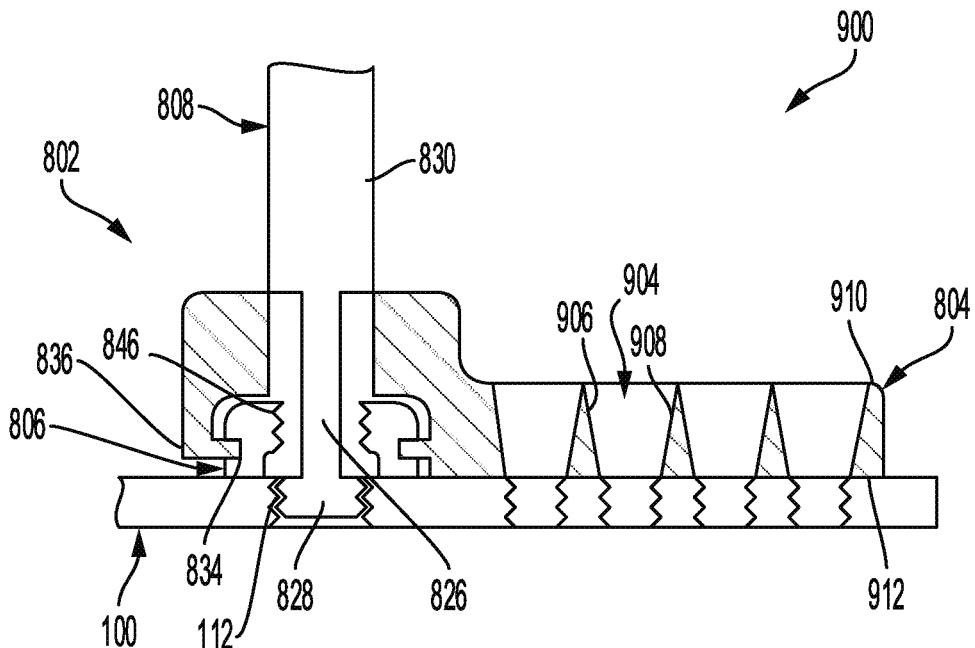
FIG. 9A illustrates a cross-sectional view of an alternative embodiment of the system shown in FIG. 8B, according to an aspect of the present disclosure.

In some aspects of the present application, one or more of the openings 812 on the guide component 804 may be shaped such that a surgeon may adjust an angle at which the surgeon installs a screw into a clavicle through such one or more openings 812. For example, FIG. 9A illustrates a cross-sectional view of an example system 900 including an anterior clavicle plate 100 and an example instrument 802 having a guide component 804 with angled openings 904. Only one opening 904 is indicated with reference numerals, though it should be appreciated that the following description applies equally to both illustrated openings 904. The indicated opening 904 is shaped with angled surfaces 906 and 908 such that the opening 904 has a larger cross sectional area at a first side 910 of the guide component 804 than at a second side 912 of the guide component 804. As such, the shape of the opening 904 enables a surgeon to advance a screw equidistant from both angled surfaces 906 and 908, or to angle a screw towards the angled surface 906 or towards the angled surface 908 when advancing the screw.

Figure 9B:
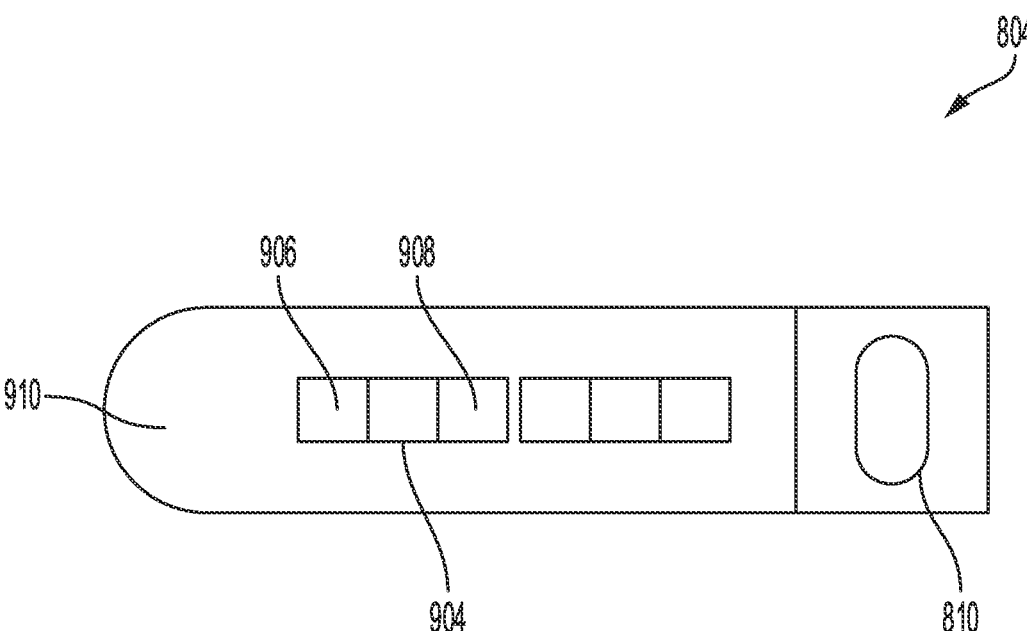
FIG. 9B illustrates a top view of the guide component shown in FIG. 9A, according to an aspect of the present disclosure.

FIG. 9B illustrates a top view of the example guide component 804 shown in FIG. 9A having angled openings 904. As shown in FIG. 9B, in some examples, the opening 904 may have a rectangular or rounded rectangular cross section from the first side 910 to the second side 912. In at least some aspects, this rectangular or rounded rectangular shape enables a surgeon to adjust the angle of a screw only along a single axis (e.g., the long side of the opening 904). In some aspects, adjacent openings 904 may join together at the first side 910 due to this shape. In such aspects in which the guide component 804 has angled openings 904, a surgeon may adjust a screw trajectory in the superior/inferior direction of the clavicle by adjusting the guide component 804 as described above, and may adjust a screw trajectory in the lateral/medial direction of the clavicle by angling the screw within the angled opening 904. The instrument 802 therefore can help provide surgeons with increased flexibility over typical systems for the trajectories at which they insert screws when installing the provided anterior clavicle plate. The increased screw trajectory flexibility can, in some instances, help surgeons achieve greater compression across a clavicle fracture than typical systems.

In at least some instances, clavicle plates installed on the superior surface of a clavicle ("superior clavicle plates") can offer better lateral fixation than anterior clavicle plates because a superior clavicle plate enables the installation of screws into a clavicle in the superior/inferior direction of the clavicle. To help provide at least some of these same benefits offered by a superior clavicle plate, in some aspects of the present application, the provided anterior clavicle plate may include an arm extending from the anterior clavicle plate's contoured body to enable fixation on a clavicle's superior surface. Such aspects of the provided anterior clavicle plate including an arm for superior surface fixation can provide the low-profile, improved contour benefits of the anterior clavicle plate 100 described above with at least some of the lateral fixation benefits of a superior clavicle plate.

Figure 10:
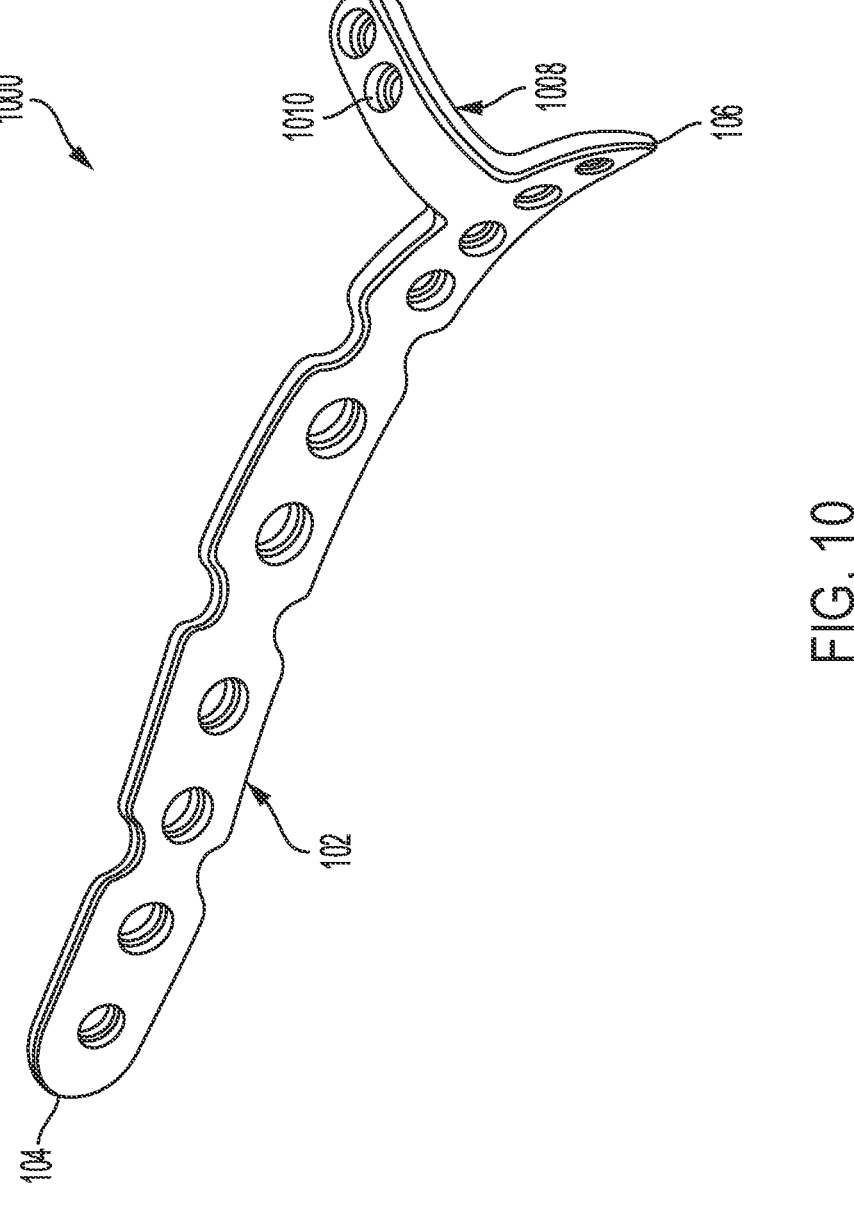
FIG. 10 illustrates a perspective view of an anterior clavicle fracture fixation plate having an arm, according to an aspect of the present disclosure.

FIG. 10 illustrates a perspective view of an example anterior clavicle plate 1000 having an arm 1008. The anterior clavicle plate 1000 includes a contoured body 102 having a first end 102 opposite a second end 106. In various aspects, the anterior clavicle plate 1000 includes an arm 1008 extending from the contoured body 102. The arm 1008 may extend substantially perpendicularly from the contoured body 102 or at another suitable angle. In some aspects, the arm 1008 may be curved such that it is centered, or substantially centered, about a single plane.

The arm 1008 includes one or more openings 1010 configured such that a screw may be inserted through a respective opening 1010. In some aspects, at least some of the one or more openings 1010 may be threaded to engage with a screw's threading. In some examples, the arm 1008 may be located on the contoured body 102 where it is illustrated, though in other examples, the arm 1008 may be located at other suitable locations along the contoured body 102. In some examples, the anterior clavicle plate 1000 may include more than one arm 1008.

The example anterior clavicle plate 1000 may include any one or more of the aspects described above in connection with the anterior clavicle plate 100. For example, while the anterior clavicle plate 1000 is shown without a guide 118 or angled opening 120, the anterior clavicle plate 1000 may include one or more guides 118 and/or angled openings 120 in other examples.

Figure 11:
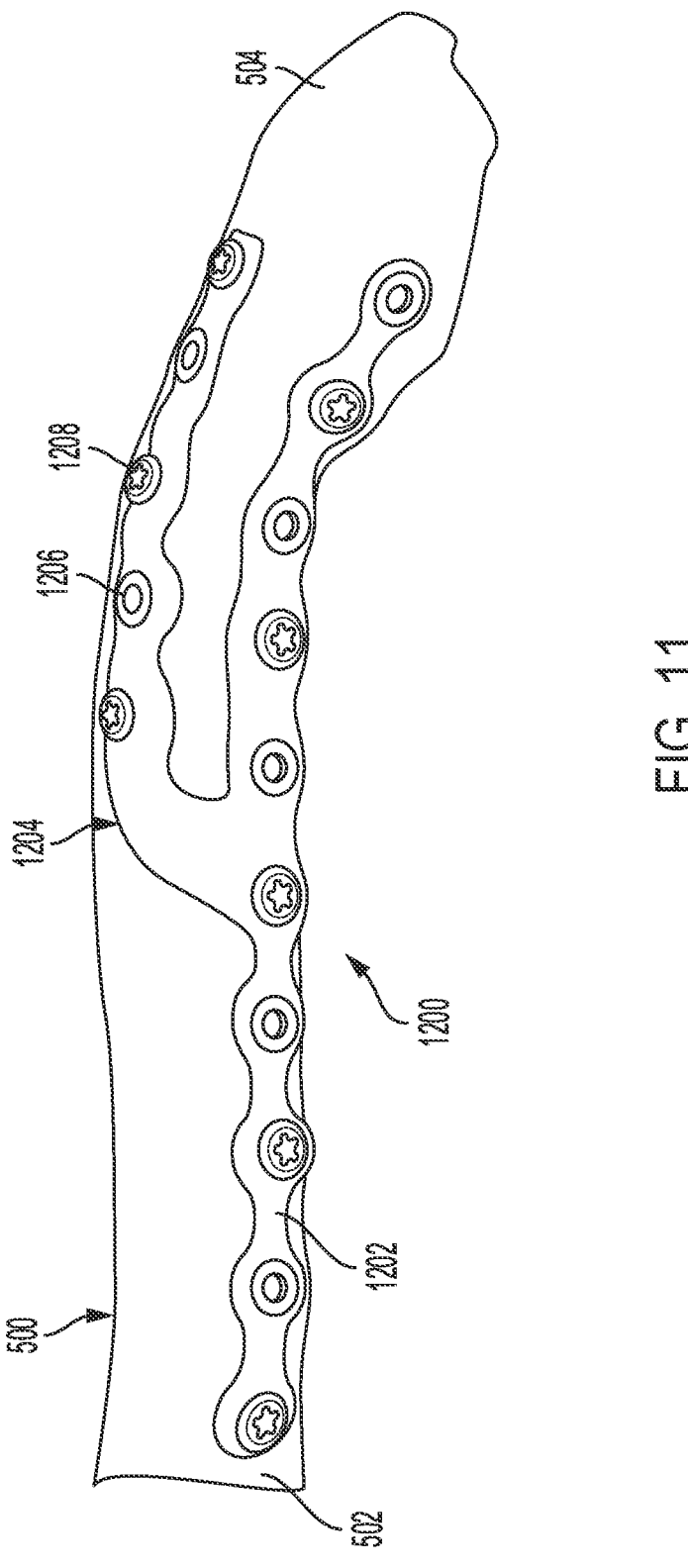
FIG. 11 illustrates a perspective view of an anterior clavicle fracture fixation plate having an arm that includes a portion substantially parallel to the plate, according to an aspect of the present disclosure.

In some examples, an arm of the provided anterior clavicle plate may extend laterally in any direction on the superior surface 504 of the clavicle 500, as compared to the arm 1008 which does not. For example, FIG. 11 illustrates a perspective view of an example anterior clavicle plate 1200 having an arm 1204 extending laterally on the superior surface 504 of the clavicle 500. The lateral extension of the arm 1204 can help provide additional lateral fixation from the superior surface 504 as compared to the arm 1008. In some examples, such as the one illustrated, a portion of the arm 1204 is substantially parallel to the contoured body 1202 as the arm 1204 extends laterally on the superior surface 504.

Similar to the example arm 1008 described above, the example arm 1204 may include a plurality of openings (e.g., the opening 1206) aligned with the superior surface 504. A screw (e.g., the screw 1208) may be driven through the openings and into the superior surface 504 of the clavicle 500. Only one opening 1206 and one screw 1208 are indicated with a reference numeral solely for illustrative clarity, and therefore it should be appreciated that the description of the openings 1206 and the screw 1208 apply equally to all those illustrated. In some aspects, at least some of the one or more openings 1206 may be threaded to engage with a screw's threading.

In various aspects, the example anterior clavicle plate 1200 may include any one or more of the aspects described above in connection with the anterior clavicle plate 100. For example, while the anterior clavicle plate 1200 is shown without a guide 118 or angled opening 120, the anterior clavicle plate 1200 may include one or more guides 118 and/or angled openings 120 in other examples.

Figure 12:
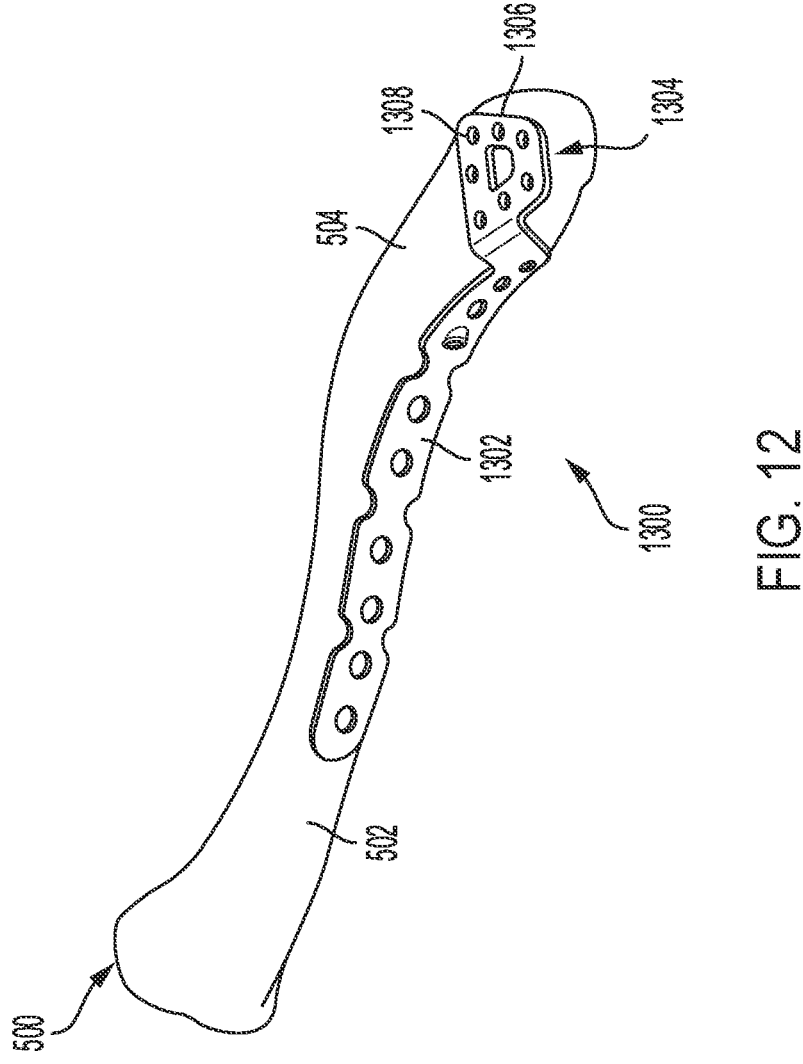
FIG. 12 illustrates a perspective view of an anterior clavicle fracture fixation plate having an arm that includes a plate, according to an aspect of the present disclosure.

In another example of the present disclosure, the provided anterior clavicle plate may have an arm that includes a plate having multiple openings for screws. For example, FIG. 12 illustrates a perspective view of an example anterior clavicle plate 1300 having an arm 1304 that includes a plate 1306. The arm 1304 extends from the contoured body 1302 of the anterior clavicle plate 1300 such that the plate 1306 is aligned substantially with the superior surface 504 of the clavicle 500.

In various aspects, the plate 1306 includes multiple (e.g., 4, 5, 6, 7, 8, etc.) openings 1308. Only one opening 1308 of the plate 1306 is indicated with a reference numeral solely for illustrative clarity. In some aspects, at least some of the multiple openings 1306 may be threaded to engage with a screw's threading. The plate 1306 can provide a higher density of openings 1308, and therefore a higher density of screws, at a particular location of the superior surface 504 of the clavicle 500 than the example arms 1008 and 1204. A high density of screws may be beneficial for fixation of a fracture at a lateral portion of the clavicle 500.

The example anterior clavicle plate 1300 may include any one or more of the aspects described above in connection with the anterior clavicle plate 100. For example, while the anterior clavicle plate 1300 is shown without a guide 118 or angled opening 120, the anterior clavicle plate 1300 may include one or more guides 118 and/or angled openings 120 in other examples.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. An anterior clavicle fracture fixation plate comprising:
a contoured body including a first end opposite a second end along a length of the contoured body, a superior side opposite an inferior side, and a plurality of openings along the length of the contoured body from the first end to the second end, each of the plurality of openings extending through a thickness of the contoured body from the superior side to the inferior side,
wherein a plane extends through a first portion of the contoured body, the first portion being adjacent the first end, and a second portion of the contoured body curves away from the plane in a first direction, the second portion of the contoured body being adjacent the second end,
wherein the contoured body includes a first bend along its length that bends at least partially in a second direction perpendicular to the first direction,
wherein a height of the contoured body, measured perpendicular to the length, is greater at the first end than at the second end,
wherein a cross-section of the contoured body is curved from the superior side to the inferior side,
wherein, for at least a segment of the contoured body, a thickness of an inferior side portion of the contoured body is greater than a thickness of a superior side portion of the contoured body, the thickness measured perpendicular to the length of the contoured body,
wherein the thickness of the superior side portion of the contoured body is greater at the first end than the second end, and
wherein the plurality of openings comprises at least one opening at the first bend and angled with respect to the thickness of the contoured body at an angle that is different than a remainder of the plurality of openings, the at least one opening allowing a screw to be inserted through the at least one opening at a non-perpendicular angle relative to the thickness of the contoured body.

2. The anterior clavicle fracture fixation plate of claim 1, wherein the contoured body includes a second bend that bends at least partially in a third direction opposite the second direction.

3. The anterior clavicle fracture fixation plate of claim 2, wherein the first bend is closer to the second end than the second bend, and wherein the first bend has a larger degree of bend than the second bend.

4. The anterior clavicle fracture fixation plate of claim 1, wherein the height of the contoured body gradually decreases along its length.

5. The anterior clavicle fracture fixation plate of claim 1, wherein a first portion of the plurality of openings have greater respective diameters than a second portion of the plurality of openings, wherein the first portion of the plurality of openings are closer to the first end of the contoured body than the second portion of the plurality of openings.

6. The anterior clavicle fracture fixation plate of claim 5, wherein the respective diameters of the plurality of openings along the length of the contoured body decrease from the first end to the second end.

7. The anterior clavicle fracture fixation plate of claim 1, further comprising an arm extending from the contoured body, the arm configured to contact a superior surface of a clavicle while the contoured body contacts a lateral surface of the clavicle.

8. The anterior clavicle fracture fixation plate of claim 7, wherein the arm extends perpendicularly from the contoured body.

9. The anterior clavicle fracture fixation plate of claim 7, wherein a portion of the arm is substantially parallel to the second end of the contoured body.

10. The anterior clavicle fracture fixation plate of claim 7, wherein the arm includes a plate having a plurality of openings.

11. The anterior clavicle fracture fixation plate of claim 1, wherein the angle is acute or obtuse.

12. The anterior clavicle fracture fixation plate of claim 1, further comprising a guide for the at least one opening, the guide protruding from a surface of the contoured body surrounding the at least one opening to aid in inserting the screw concentrically in the at least one opening.

13. A system for clavicle fracture fixation comprising:
an anterior clavicle fracture fixation plate including:
a contoured body including a first end opposite a second end along a length of the contoured body, a superior side opposite an inferior side, and a plurality of openings along the length of the contoured body from the first end to the second end, each of the plurality of openings extending through a thickness of the contoured body from the superior side to the inferior side,
wherein a plane extends through a first portion of the contoured body, the first portion being adjacent the first end, and a second portion of the contoured body curves away from the plane in a first direction, the second portion of the contoured body being adjacent the second end,
wherein the contoured body includes a first bend along its length that bends at least partially in a second direction perpendicular to the first direction,
wherein a height of the contoured body, measured perpendicular to the length, is greater at the first end than at the second end,
wherein a cross-section of the contoured body is curved from the superior side to the inferior side,
wherein, for at least a segment of the contoured body, a thickness of an inferior side portion of the contoured body is greater than a thickness of a superior side portion of the contoured body, the thickness measured perpendicular to the length of the contoured body,
wherein the thickness of the superior side portion of the contoured body is greater at the first end than the second end, and
wherein the plurality of openings comprises at least one opening at the first bend and angled with respect to the thickness of the contoured body at an angle that is different than a remainder of the plurality of openings, the at least one opening allowing a screw to be inserted through the at least one opening at a non-perpendicular angle relative to the thickness of the contoured body; and
an instrument configured to aid in insertion of one or more screws through openings of the anterior clavicle fracture fixation plate on an anterior surface of a clavicle.

14. The system of claim 13, wherein the instrument includes:
a base member configured to contact the anterior clavicle fracture fixation plate,
a guide member including a slot and an elongate portion having a plurality of openings, and
a locking post,
wherein the locking post is positioned through the slot of the guide member and through the base member, thereby coupling the guide member and the base member.

15. The system of claim 14, wherein prior to engaging the locking post to the anterior clavicle fracture fixation plate, the guide member is rotatable about a long axis relative to the base member, and wherein subsequent to engaging the locking post to the anterior clavicle fracture fixation plate, the guide member is fixed relative to the base member.

16. The system of claim 14, wherein the guide member includes a first face configured to be adjacent to the anterior clavicle fracture fixation plate and a second face opposite the first face, and wherein the plurality of openings of the guide member include a greater cross sectional area at the second face than at the first face.

17. The system of claim 13, wherein the contoured body of the anterior clavicle fracture fixation plate is contoured such that it conforms to one of an anterior surface of a right side clavicle of a patient or an anterior surface of a left side clavicle of the patient.

18. A method for fixing a fracture of a clavicle comprising:

installing an anterior clavicle fracture fixation plate on at least an anterior surface of the clavicle, the anterior clavicle fracture fixation plate including:

a contoured body including a first end opposite a second end along a length of the contoured body, a superior side opposite an inferior side, and a plurality of openings along the length of the contoured body from the first end to the second end, each of the plurality of openings extending through a thickness of the contoured body from the superior side to the inferior side, wherein a plane extends through a first portion of the contoured body, the first portion being adjacent the first end, and a second portion of the contoured body curves away from the plane in a first direction, the second portion of the contoured body being adjacent the second end, wherein the contoured body includes a first bend along its length that bends at least partially in a second direction perpendicular to the first direction, wherein a height of the contoured body, measured perpendicular to the length, is greater at the first end than at the second end, wherein a cross-section of the contoured body is curved from the superior side to the inferior side, wherein, for at least a segment of the contoured body, a thickness of an inferior side portion of the contoured body is greater than a thickness of a superior side portion of the contoured body, the thickness measured perpendicular to the length of the contoured body, wherein the thickness of the superior side portion of the contoured body is greater at the first end than the second end, wherein the plurality of openings comprises at least one opening at the first bend and angled with respect to the thickness of the contoured body at an angle that is different than a remainder of the plurality of openings, and wherein installing the anterior clavicle fracture fixation plate includes inserting respective screws through each of the plurality of openings and into the clavicle, one screw being disposed through the at least one opening at a non-perpendicular angle relative to the thickness of the contoured body.

19. The method of claim 18, wherein at least some of the respective screws are inserted into the clavicle at an acute or obtuse angle relative to the contoured body.

20. The method of claim 18, wherein installing the anterior clavicle fracture fixation plate on at least the anterior surface of the clavicle includes, prior to inserting respective screws through each of the plurality of openings, aligning respective axes of the plurality of openings of the anterior clavicle fracture fixation plate with the clavicle via an instrument coupled to the anterior clavicle fracture fixation plate.

* * * * *